United States Patent [19]

Castellano et al.

[11] Patent Number: 5,606,974
[45] Date of Patent: Mar. 4, 1997

[54] CATHETER HAVING ULTRASONIC DEVICE

[75] Inventors: Thomas M. Castellano, Temecula; Robert C. Hayzelden, Canyon Lake; Tracy D. Maahs, San Jose, all of Calif.

[73] Assignee: Heart Rhythm Technologies, Inc., Temecula, Calif.

[21] Appl. No.: 434,004

[22] Filed: May 2, 1995

[51] Int. Cl.$^6$ ..................................... A61B 8/12
[52] U.S. Cl. ....................................... 128/662.06
[58] Field of Search ............... 128/662.03, 662.06; 607/97, 101, 102; 601/2, 3; 604/22

[56] References Cited

U.S. PATENT DOCUMENTS

| | | | |
|---|---|---|---|
| 3,075,515 | 1/1963 | Richards | 128/2.05 |
| 3,232,794 | 2/1966 | Korton | 136/4 |
| 3,336,804 | 8/1967 | Poppendiek et al. | 73/204 |
| 3,359,974 | 12/1967 | Khalil | 128/2.05 |
| 3,438,253 | 4/1969 | Kuether et al. | 73/204 |
| 3,595,079 | 7/1971 | Grahn | 73/204 |
| 3,893,058 | 7/1975 | Keith | 338/28 |
| 3,938,502 | 2/1976 | Bom | 128/2 V |
| 4,075,036 | 2/1978 | Lysikov et al. | 136/225 |
| 4,253,469 | 3/1981 | Aslan | 128/736 |
| 4,411,266 | 10/1983 | Cosman | 128/303.18 |
| 4,706,681 | 11/1987 | Breyer et al. | 128/642 |
| 4,745,928 | 5/1988 | Webler et al. | 128/692 |
| 4,749,415 | 6/1988 | Barton | 136/230 |
| 4,841,981 | 6/1989 | Tanabe et al. | 128/692 |
| 4,869,248 | 9/1989 | Narula | 128/303.13 |
| 4,901,734 | 2/1990 | Griffin et al. | 128/692 |
| 4,936,281 | 6/1990 | Stasz | 128/660.03 |
| 4,960,109 | 10/1990 | Lele | 128/736 |
| 5,002,059 | 3/1991 | Crowley et al. | 128/662.06 |
| 5,070,882 | 12/1991 | Bui et al. | 128/662.06 |
| 5,174,299 | 12/1992 | Nelson | 128/692 |
| 5,176,141 | 1/1993 | Bom et al. | 128/662.06 |
| 5,228,176 | 7/1993 | Bui et al. | 29/25.35 |
| 5,269,291 | 12/1993 | Carter | 128/24 AA |
| 5,271,410 | 12/1993 | Wolzinger et al. | 128/692 |
| 5,295,484 | 3/1994 | Marcus et al. | 128/660.03 |
| 5,304,115 | 4/1994 | Pflueger et al. | 604/22 |
| 5,312,328 | 5/1994 | Nita et al. | 604/22 |
| 5,363,853 | 11/1994 | Lieber et al. | 128/662.06 |
| 5,385,148 | 1/1995 | Lesh et al. | 128/662.06 |
| 5,385,544 | 1/1995 | Edwards et al. | 607/101 |
| 5,391,197 | 2/1995 | Burdette et al. | 607/97 |
| 5,405,346 | 4/1995 | Grundy et al. | 606/41 |
| 5,423,808 | 6/1995 | Edwards et al. | 606/34 |

FOREIGN PATENT DOCUMENTS

WO93/087555  5/1993  WIPO ............... A61B 17/36

*Primary Examiner*—George Manuel
*Attorney, Agent, or Firm*—Fulwider Patton Lee & Utecht, LLP

[57] ABSTRACT

A catheter includes a piezoelectric transducer mounted to the distal end of a catheter. In one embodiment, the piezoelectric transducer has the shape of a cylinder and in another embodiment, a convex shape with a mounting flange. In the cylindrical shape, a plurality of surface mounted temperature sensors are disposed within the piezoelectric transducer. The sensors are electrically insulated and a sealing technique prevents the leakage of body fluids from penetrating the interior of the catheter through the sensor bores. The cylindrical transducer is supported on mounting members so that it is accurately mounted and sealed while at the same time, the material used does not significantly dampen the transducer. The convex shape includes a temperature sensor at its tip.

24 Claims, 5 Drawing Sheets

CATHETER HAVING ULTRASONIC DEVICE

BACKGROUND

The invention is generally related to devices for sensing physiological parameters and, more particularly, to catheters having an ultrasonic device.

The heart beat in a healthy human is controlled by the sinoatrial node ("S-A node") located in the wall of the right atrium. The S-A n electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of or damage to the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as cardiac arrhythmia.

Electrophysiological ablation is a procedure often successful in terminating cardiac arrhythmia. This procedure involves applying sufficient energy to the interfering tissue to ablate that tissue thus removing the irregular signal pathway. However, before an ablation procedure can be carried out, the interfering tissue must first be located.

One location technique involves an electrophysiological mapping procedure whereby the electrical signals emanating from the conductive endocardial tissues are systematically monitored and a map is created of those signals. By analyzing that map, the interfering electrical pathway can be identified. A conventional method for mapping the electrical signals from conductive heart tissue is to percutaneously introduce an electrophysiology ("EP") catheter having mapping electrodes mounted on its distal extremity. The catheter is maneuvered to place those electrodes in contact with or in dose proximity to the endocardium of the patient's heart. By monitoring the electrical signals at the endocardium, aberrant conductive tissue sites responsible for the arrhythmia can be pinpointed.

Once the origination point for the arrhythmia is located in the tissue, the physician may use an ablation procedure to destroy the tissue causing the arrhythmia in an attempt to remove the electrical signal irregularities and restore normal heart beat or at least an improved heart beat. Successful ablation of the conductive tissue at the arrhythmia initiation site usually terminates the arrhythmia or at least moderates the heart rhythm to acceptable levels.

The distal end of an EP catheter may include mapping electrodes as well as an ablation device for performing the ablation procedure. One type of ablation device includes an ablation electrode that emits radio frequency ("RF") energy to heat the target tissue to a temperature high enough to cause ablution of that tissue. Other types of ablation devices may be used and in the following disclosure, an ultrasonic device is disclosed.

As the ablation procedure progresses, heat is generated and the surrounding blood is exposed to this heat. At approximately 100° C., charring and boiling of the blood take place. Charring is particularly troublesome at the surface of the ablation device because emboli may form on the surface of the device to an extent that the catheter must be removed and cleaned before the procedure can continue. Furthermore, in RF ablation procedures, charring and boiling of the blood seriously modify the electrical conductivity of blood and tissue and cause an increase in the overall electrical impedance of the electrical heating circuit and a drop in the power delivery to the tissue. Too great a rise in impedance can result in sparking and thrombus formation within the heart, both of which are undesirable.

Although no significant amount of heat is generated in the ablation device itself, adjacent heated endocardial tissue will heat the ablation device via heat conduction through the tissue. Because part of the active transducer is in contact with the blood in the heart, blood boiling, emboli development, and clotting can result if the surface temperature of the transducer exceeds 90°–100° C. If this occurs, the ablution procedure must be stopped regardless of whether the entire ablation procedure has been completed. The catheter must then be removed from the patient, the attached necrotic tissue removed, and the catheter reinserted into the patient. Such cleaning processes require extra time and unduly prolong the ablation procedure. To avoid such undesirable circumstances, a temperature sensor may be incorporated at the distal end of the catheter to monitor and maintain a selected temperature during ablation. The ablation process can then be controlled so that the temperature is not allowed to increase above a predetermined level.

Temperature sensors have been incorporated in catheters for some time. In some cases, these prior temperature sensors were mounted at particular points inside the catheter body. While perhaps suitable for some applications, such a mounting scheme is less desirable for EP applications. The surrounding body of the catheter will insulate the temperature sensor from the tissue heat and will also impose a delay in heat transfer. More time to stabilize will be required thus slowing sensor response time. The tissue and blood temperatures may actually be greater than the internal sensor indicates.

Another approach involves mounting temperature sensors externally on the catheter body. Some of these temperature sensors comprise thermocouples having elongated leads for sending temperature signals to the proximal end of the catheter. However, when a thermocouple and its leads are mounted to the outer surface of the catheter body, the diametric profile of the catheter body is undesirably increased and in some cases, difficulty is encountered in securely mounting such a structure externally. In the case where the EP catheter utilizes an ultrasonic transducer for ablation, it is more difficult to mount a temperature sensor in the transducer itself. Ultrasonic transducers are typically composed of relatively brittle piezoelectric crystalline material that is somewhat fragile and fracturable. Attempting to mechanically drill through the crystalline structure can cause fractures in the structure that may leak body fluids into the catheter interior, or may eventually cause the crystal itself to fail. This characteristic has made it difficult to mount temperature sensors at the surface of the ultrasonic transducer and instead, such sensors have typically been mounted at a position proximal to the crystal. This of course delays the sensor's response to temperatures located at the distal tip of the catheter and for that reason, is undesirable.

When used in a percutaneous ablation procedure, it is sometimes difficult to closely control the orientation of the distal end of the catheter. If a "side-fire" type of ablation device is used, only a pan of the circumference of the device will be in contact with the tissue to be ablated. If the distal end should include only a single temperature sensor, that sensor may provide an accurate temperature indication if it is in contact with the tissue. However, if the distal end of the catheter is oriented such that the sensor is positioned in the cooler flowing blood, its temperature indication may not be as high as the temperatures of other parts of the ablation device. Blood boiling, emboli creation, and clotting may actually be occurring while going undetected.

A similar situation may occur in the case of an "end-fire" ablation device. If the temperature sensor is located at a position removed from the ablation device, it may indicate a temperature lower than the hotter device.

As used herein, a "side-fire" device is one that is mounted such that it conducts energy sideways in relation to the catheter shaft. An "end-fire" device is one that is mounted such that it conducts energy at the distal end of the catheter in relation to the catheter shaft.

A further problem encountered in working with ultrasonic transducers is their tendency to "pump" fluids through any openings associated with them. The physical movement of the transducer as it is performing its transducing function on the tip of a catheter for instance, can cause body fluids to enter the interior of the catheter through openings in the transducer unless careful sealing measures have been used to seal the transducer openings. The entrance of body fluids can cause a damping effect on the ultrasonic crystal causing it to become less effective in providing ablation energy.

Hence, those skilled in the art have recognized the need for a temperature sensing device or devices mounted at the distal end of an electrophysiology ablation catheter that is configured to provide a more rapid response time and accurate temperature indication. The ultrasonic transducer and catheter should provide a mounting configuration that provides for securely mounting the transducer to the distal end of the catheter tube without any undue ultrasonic damping. Such mounting configuration should provide for an effective seal so that body fluids do not enter the catheter and affect the operation of the transducer. Additionally, these temperature sensors should be relatively small so that the sensor does not interfere with the effective operation of the ablation device and response time is shortened. In addition, the temperature sensor should be relatively inexpensive to manufacture and reliable in use. The present invention fulfills these needs and others.

SUMMARY OF THE INVENTION

Briefly and in general terms, the present invention is directed to a catheter having an ultrasonic transducer mounted at the distal end thereof. In one aspect of the invention, the ultrasonic transducer has the form of a cylindrical tube with multiple sensor holes formed through the side wall of the transducer. Temperature sensing devices are mounted in the holes for monitoring temperatures to which the catheter is exposed. The ultrasonic transducer is mounted at a position proximal to the distal tip so that a side-fire transducer is formed.

In a different aspect, the ultrasonic transducer has the form of convex-shaped tip and is mounted to the distal tip of the catheter shaft to form an "end-fire" transducer. A sensor hole is formed in the ultrasonic transducer and a temperature sensor is mounted in the hole.

In a further aspect, an elastomeric sheath, fitted tightly into each sensor's hole, functions to isolate the sensing device from the ultrasonic transducer and acts as a strain relief for the sensor's leads. The temperature sensing device is received within the sheath and an adhesive is applied therein to affix the temperature sensing device within the sensor hole and anchor it to the outer surface of the transducer. The adhesive encapsulates the temperature sensing device sealing it from the entry of body fluids and in addition, prevents it from being pulled into the interior of the transducer. In one aspect, the adhesive comprises a matching or conformal layer that coats the entire outer surface of the ultrasonic transducer.

In yet a further aspect, the insulation surrounding the thermocouple leads may be made larger so that they more snugly fit within the hole through the transducer, the thicker insulation acting as an electrical isolator and as a strain relief.

In yet another aspect of the invention, the temperature sensing device is mounted in the sensor hole, such that the outer extremity of the sensing device is positioned substantially even with the outer surface of the ultrasonic transducer including a matching layer.

In the cylindrically-shaped transducer, mounting "O-rings" support, position, and isolate the air-backed ultrasonic transducer without causing undue damping of its transducing movements. The O-rings comprise a low durometer material so that the transducer is not significantly damped.

In another aspect of the invention, the cylindrical transducer is disposed on a base between the shaft of the catheter and a tip electrode. Sealant beads located between the shaft and the transducer and between the electrode tip and the transducer isolate and support the transducer. Each sealant bead comprises a low durometer, biocompatible, adhesive/sealant that also is of sufficient hardness so that it does not damp the transducer significantly. The beads prevent body fluids and other fluids from entering the interior of the catheter around the ultrasonic transducer.

In a more detailed aspect in relation to the cylindrical transducer, the wall of the cylindrical transducer comprises three sensors spaced equiangularly apart. In a very particular aspect, the three sensors are spaced 120 degrees apart in a common plane.

In another aspect, the ultrasonic transducer in the form of a hollow, distally projecting convex-shaped tip is integrally formed with a proximally extending tubular cylindrical portion functioning as a mounting flange. The mounting flange is extended so as to provide a relatively large surface area for an adhesive/sealant to attach the transducer to the end of the catheter.

Other features and advantages of the invention will become apparent from the following detailed description taken in conjunction with the accompanying drawings, which illustrate by way of example, the features and advantages of the invention.

DETAILED DESCRIPTION OF THE PREFERRED EMBODIMENTS

Figures 1, 6, 7:
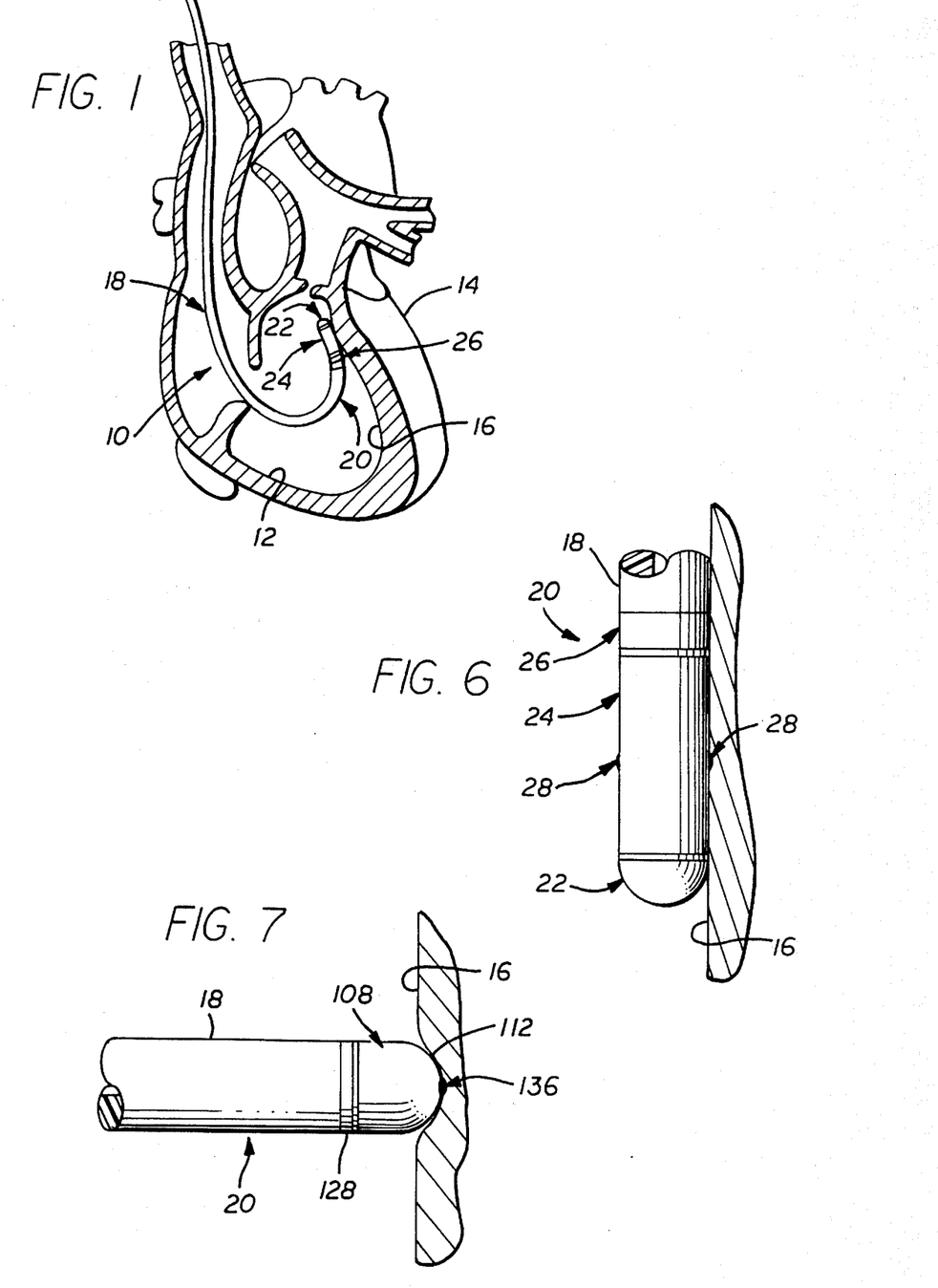
FIG. 1 is a diagrammatic view of a human heart in partial section showing an EP catheter disposed internally and located so that one side of a "side-fire" energy transducer mounted at its distal end is against the endocardium for performing an electrophysiological procedure, the catheter including temperature sensing devices in accordance with the present invention.
FIG. 6 is a side view of the catheter of FIG. 2 showing its distal end disposed parallel to and in contact with an ablation site for side-fire use.
FIG. 7 is a side view of the catheter of FIG. 6 showing its distal end disposed perpendicularly to and in contact with an ablation site for "end-fire" use.

In the following description, like reference numerals will be used to refer to like or corresponding elements in the different figures of the drawings. Referring now to FIG. 1 in more detail, an electrophysiology ("EP") type catheter 10 is shown inserted into the right ventricle 12 of a human heart 14 for localized diagnosis or treatment of the endocardial tissue 16 thereof. The catheter includes, in this case, an elongated catheter tube or body 18 having a distal end 20 with an electrode 22 mounted at the distal tip, a cylindrical ultrasonic transducer 24, in this case a piezoelectric device, mounted proximal to the tip electrode, and a band electrode 26 mounted proximal to the piezoelectric transducer 24. The electrodes 22 and 26 and the piezoelectric transducer 24 may be individually or simultaneously actuated to perform various electrophysiological procedures. In FIG. 1, the distal end of the catheter is shown parallel to and in contact with the endocardium for performing a side-fire EP ablation procedure with the piezoelectric transducer 24.

The distal end 20 of the elongated catheter body 18 is steerable and has sufficient torsional and axial rigidity for maneuvering the distal end through the vascular system and to selected sites within the heart chamber. The catheter body 18 is of sufficient length, for instance to allow for a transluminal percutaneous brachial approach to the heart of an adult patient and/or a transluminal percutaneous femoral approach.

Figure 2:
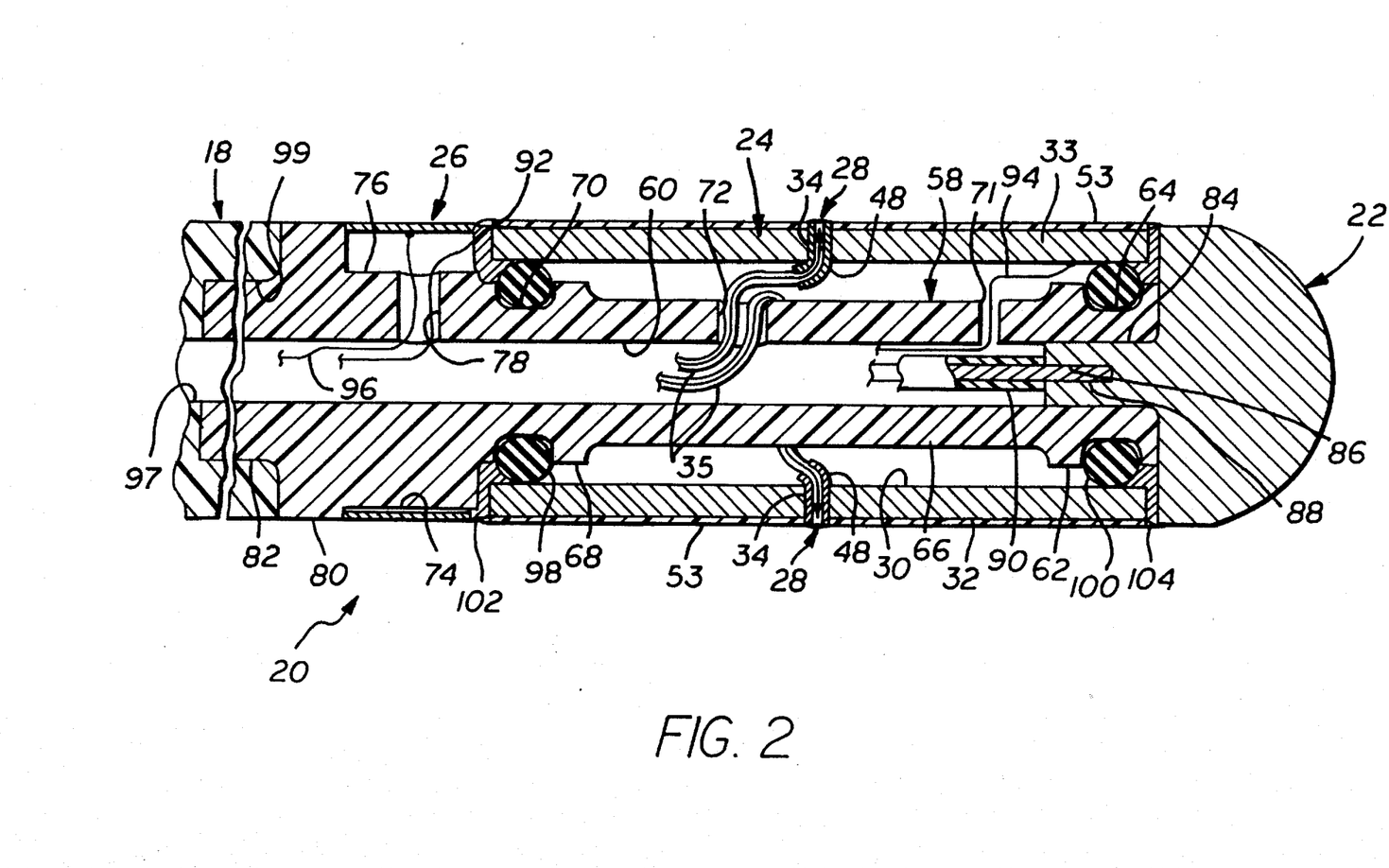
FIG. 2 is an enlarged, partially broken, cross-sectional side view of the distal end of the EP catheter shown in FIG. 1 including a piezoelectric side-fire transducer having a plurality of temperature sensing devices.

Referring now in more detail to FIG. 2, the distal tip electrode 22 may be a mapping and pacing type electrode used to send or receive electrical signals from adjacent endocardial tissue for locating aberrant conductive tissues. Suitable materials for the tip electrode 22 include pure platinum, a platinum iridium alloy such as "platinum 10 iridium" (90% platinum 10% iridium), a gold alloy, pure titanium, and/or pure tungsten. The band electrode 26, proximal to the piezoelectric transducer 24, may also be used either individually or simultaneously with the tip electrode 22 to perform EP mapping procedures.

The cylindrical piezoelectric transducer 24 directs ultrasonic acoustic energy in a radial outward direction for "side-fire" operation. When transmitting ultrasonic energy radially outward, tissue located adjacent the transducer will be ablated.

As shown in FIG. 2, a pair of temperature sensing devices 28 are mounted in the wall of the cylindrical piezoelectric transducer 24. For purposes of illustration, two sensing devices are shown; however, more or fewer sensing devices may be mounted in the transducer. In one particular embodiment, three temperature sensing devices are mounted in the transducer wall and are spaced equiangularly apart (120 degrees) in a common transverse plane. As is discussed below, having a greater number of temperature sensing devices in the transducer may be more desirable to obtain an accurate temperature indication in a side-fire application.

The cylindrical transducer 24 has inner 30 and outer surfaces 32 and sensor bore holes 34 are formed completely through those surfaces and the wall 33 of the transducer. Each of the sensing devices 28 is in the form of a point sensor mounted within the respective sensor bore hole.

The bore holes 34 may be formed through the wall of the cylindrical piezoelectric transducer by a non-mechanical contact, ultrasonic machining process available commercially. The bore holes, in one embodiment were 0.1778 mm (0.007 in) in diameter. It is desirable that the temperature sensing devices 28 be as small as possible so that when the devices are mounted in the sensor bore holes of the piezoelectric transducer 24, the transducer's ultrasonic performance is minimally affected and the temperature response times are minimized.

Figure 3:
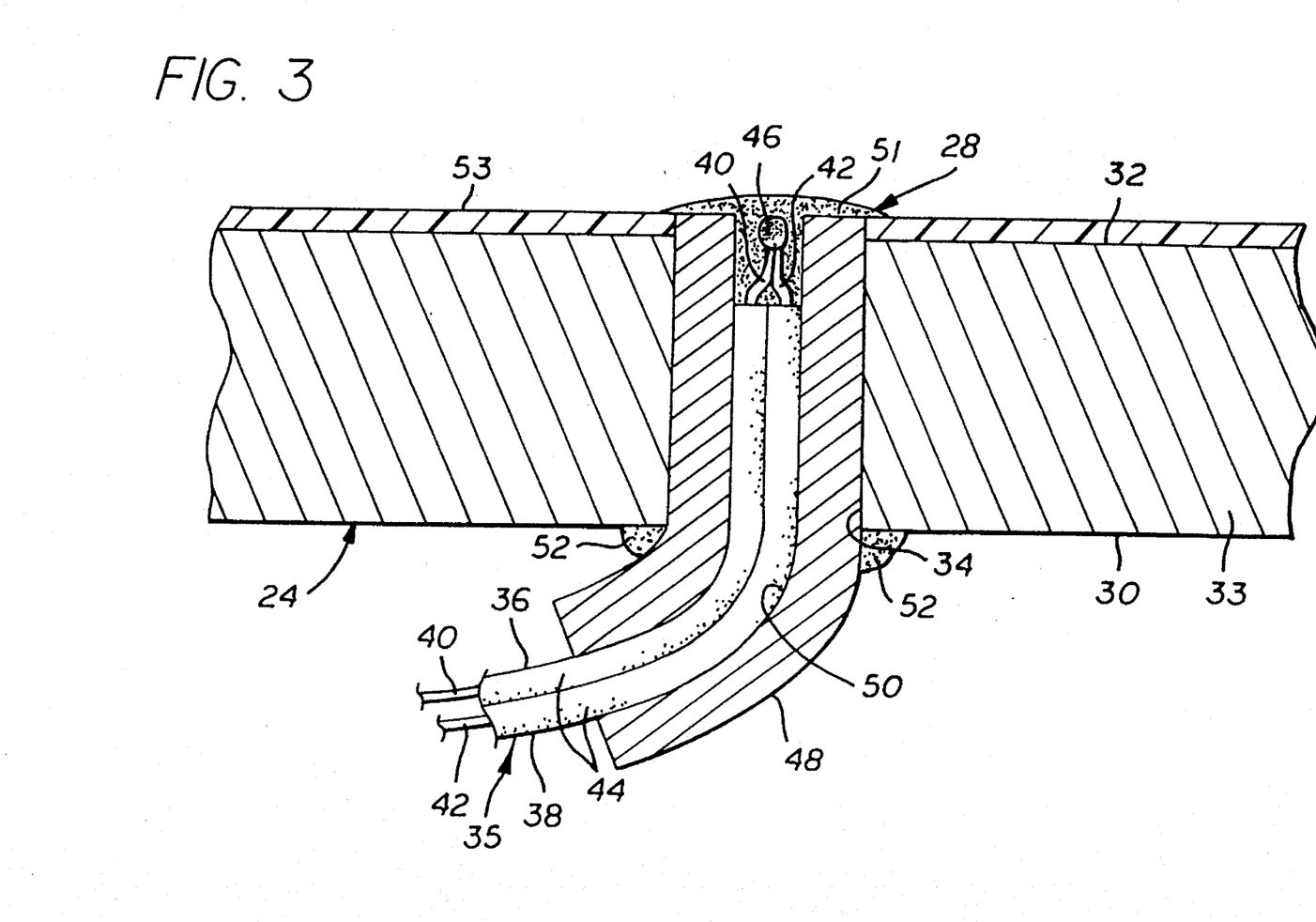
FIG. 3 is an enlarged sectional side view of one of the temperature sensing devices shown in FIG. 2 showing its mounting configuration in the catheter.
Figure 4:
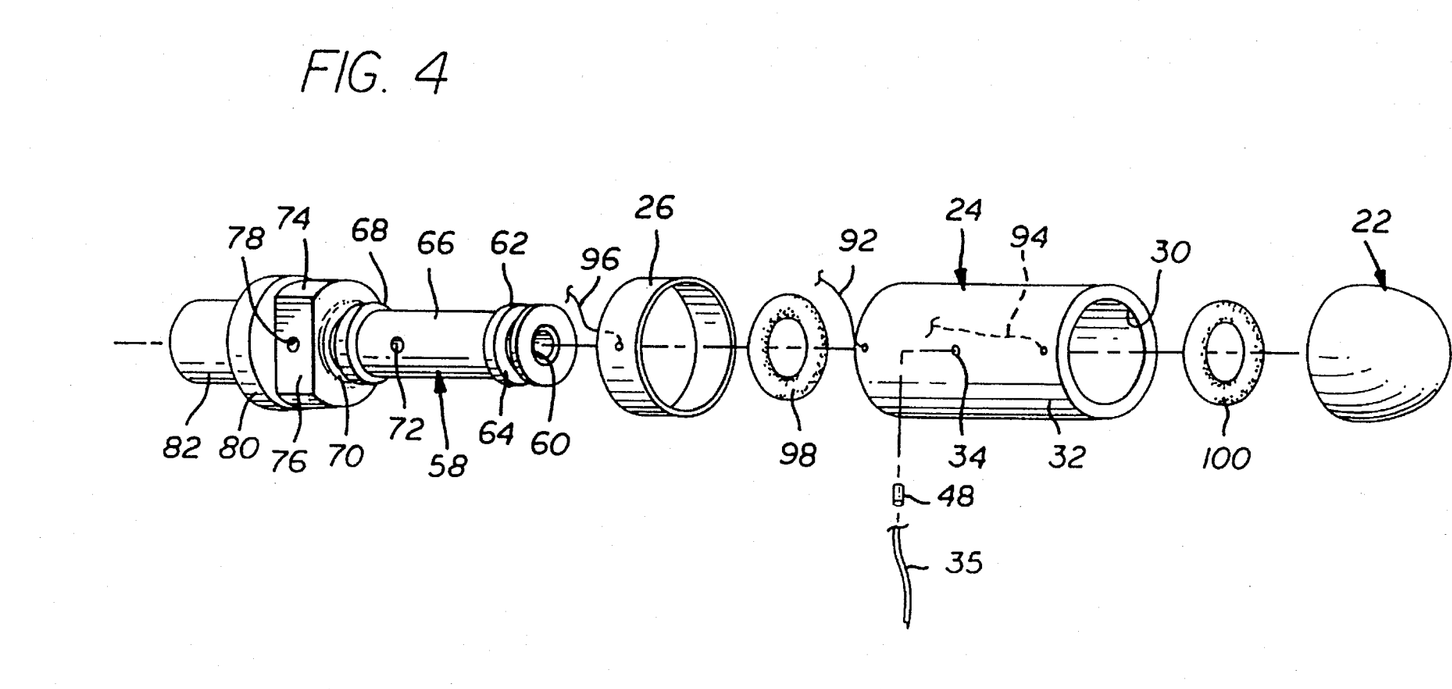
FIG. 4 is an exploded perspective view of the distal end of the EP catheter shown in FIG. 2.

Referring now to FIGS. 3 and 4, thermocouples 33 used as the temperature sensing device 28 are shown. The thermocouple includes an elongated electrical sensing lead pair 35 comprising individually insulated flexible electrical temperature sensing leads 36 and 38. The electrical leads include respective electrically conductive wires, 40 and 42, formed of dissimilar materials. The distal portion of each wire is stripped of its insulation 44 and is coupled with the stripped distal portion of the other lead to form the thermocouple. In one embodiment, one wire 40 is formed of copper and the other wire 42 is formed of constantan ("T" type). Alternatively, the thermocouple 33 may be constructed of other dissimilar metallic materials.

With particular reference to FIG. 3, the distal portions of the dissimilar wires 40 and 42 may be joined such as by welding or bonding together, for instance by conductive solder 46, to form the thermocouple junction along the length of the solder joint. The electrical temperature sensing leads 36 and 38 are formed from a forty-four gauge (AWG) bifilar wire. A bifilar wire of this sort is available from Hudson International of Trenton, Ga. and when connected as shown, it forms a T-type thermocouple 33. Alternatively, as shown in the embodiment of FIG. 4, the dissimilar metallic wires may be joined by TIG or laser welding to form an enlarged weld bead 49 defining the thermocouple junction.

In both configurations, electrical current may thus pass through the thermocouple junction to create the thermocouple effect. The opposite ends of the respective sensing leads 36 and 38 may be connected to a connector (not shown) mounted on a manipulation handle at the proximal end of the catheter. The sensing leads carry the sensing signals responsive to the temperature sensed at the thermocouple. Those sensing signals may be used by monitoring equipment to derive temperature indications.

In the embodiment shown in FIG. 3, the sensor bore hole 34 is of a uniform diameter along its length. In this embodiment, a flexible elastomeric tubular sheath 48 is provided for receipt within the sensor bore hole, the sheath having an inner bore 50 therethrough. Preferably, the tubular sheath is composed of an elastomeric polyamide having an inner bore 50 diameter sized for snug receipt of the pair of electric sensor leads 36 and 38 and having an outer diameter sized for a snug fit within the sensor bore hole 34.

To assemble the temperature sensing device 28 to the transducer 24 in the embodiment shown in FIG. 3, the sheath 48 is pulled into the sensor bore hole 34 from the outside surface 32 of the transducer. The length of the sheath is greater than the thickness of the wall of the transducer and the matching layer 53 so that an excess length protrudes inwardly from the inner surface 30 of the transducer. The outer surface of the sheath is cut or otherwise positioned such that it is flush with the outer surface of the matching layer 53. An annular bead 52 of an adhesive, such as cyanoacrylate, is applied around the periphery of the sheath along the inner surface of the transducer to secure the sheath thereto. Not only does this bead 52 anchor the sheath in the bore, but it also provides an inner fluid seal to further prevent the entry of body fluids into the interior of the catheter.

The proximal ends of the bifilar sensor leads 36 and 38 are then received through the inner bore 50 of the sheath 48 from the outside of the transducer such that the distal extremity of the thermocouple 33 is positioned substantially at the same level or flush with the outer surface of the matching layer 53 as shown in FIG. 3. Because the sheath extends inwardly past the edge of the bore 34, it provides a strain relief for the sensing thermocouple leads 36 and 38 as well as protecting them from the possible loss of their insulation layers 44 should they scrape against the transducer. Movement of the transducer occurs due to the nature of a piezoelectric transducer and such movement can be detrimental to sensor leads.

Thereafter, an adhesive 51 is applied to the thermocouple, sheath, and matching layer to seal and anchor the assembly as one as shown in FIG. 3. A crown allows the thermocouple to be mounted flush with the outer surface of the matching layer. The matching layer provides a better acoustical impedance match between the piezoelectric crystal and heart tissue for more efficient energy transfer as well as provides a biolayer and adds mechanical strength to the transducer as well.

As mentioned above, it has been found that piezoelectric transducers will effect a pumping action of fluid through an associated orifice or opening due to the movement of the transducer. Fluid entry into the interior of an EP catheter is undesirable because it may significantly damp the piezoelectric transducer's performance rendering the catheter effectively useless. The approach described above and illustrated in the accompanying figures prevents fluid entry. In the embodiment shown in FIG. 3, the use of a resilient sheath 48 compressed in the bore through the piezoelectric transducer 24 provides a first, main defense against leakage. By applying adhesive/sealant about the sheath on the outside and the inside provides further protection against leakage as well as performing other functions described above.

Figure 5:
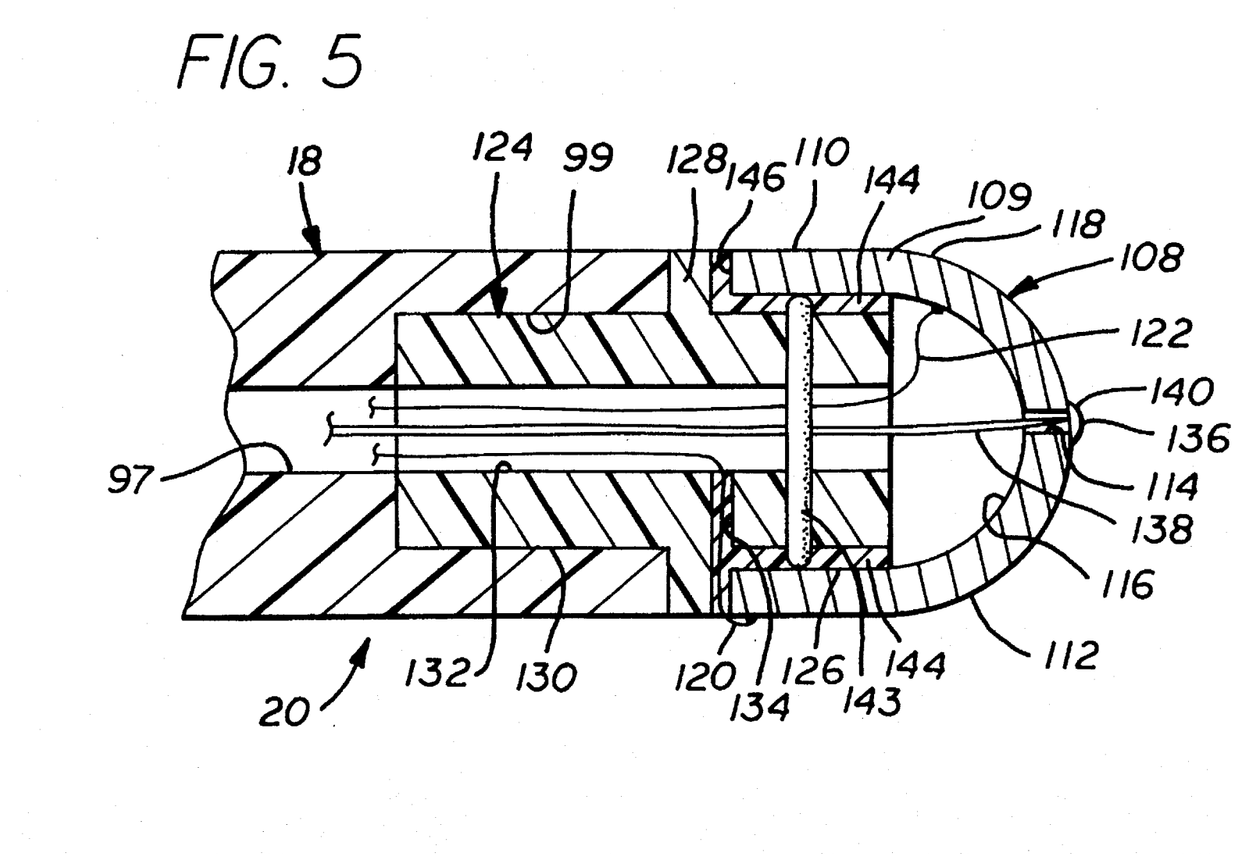
FIG. 5 is an enlarged cross sectional side view of the distal end of another embodiment of an EP catheter in which an "end-fire" ultrasonic transducer is formed with a convex-shaped tip and also includes a temperature sensing device disposed in the transducer.

With reference now to FIGS. 2 and 5, the construction of the distal end 20 of the catheter will be described including the assembly of the distal end electrode 22, the cylindrical piezoelectric transducer 24 and the band electrode 26 onto the distal end of the catheter. In general, the distal tip electrode 22, piezoelectric transducer 24, and band electrode 26 are mounted to a mounting member or base 58 and the base is mounted to the distal end of the catheter body 18.

The mounting base 58 is generally an elongated cylindrical body having a longitudinal axial bore 60 therethrough. The distal end of the base has a head 62 formed with an annular O-ring retention groove 64. The base is formed with a smaller diameter neck 66 extending in the proximal direction from the head 62 to a larger diameter flange 68 also formed with an annular O-ring retention groove 70. A radial sensor lead bore 72 is formed through the wall of the neck 66, generally at the medial portion thereof. Formed proximally from the flange 68 is a larger diameter shoulder 74 having a flat surface 76 along one side. The flat surface 76 provides room for a welding joint of an electrical lead to the electrode, as discussed below. An electrode lead bore 78 is formed from the flat surface radially inwardly to the axial bore 60. The shoulder 74, from the proximal end thereof, further expands radially to a larger diameter abutment plate 80 and is formed therefrom with a smaller diameter elongated mounting stem 82 (shown partially broken in FIG. 2). The base 58 is electrically insulative and may be formed of VLTEM for example.

The tip electrode 22, in the embodiment shown in FIGS. 2 and 5, is generally bullet-nose in shape but may take other shapes. The proximal end of the tip electrode 22 is formed with a small diameter, axially projecting mounting post 84. The proximal end of the post is formed with an axial electrode connector bore 86 for connection to an elongated electrical conductor wire 88 having an insulative jacket 90. The insulative jacket at the distal end of conductor wire 88 is stripped away and the distal tip of the wire conductor 88 is received within the connector bore 86. The conductor is affixed to the tip electrode by crimping the post 84 about the conductor or by soldering the conductor thereto, or by other means. The length of the conductor wire 88 is selected such that the conductor may extend and attach to an electrical connector at a manipulation handle (not shown) at the proximal end of the catheter 10. In the preferred configuration, the conductor wire is formed of a high strength copper beryllium that conducts electrical signals from the tip electrode to the connector at the proximal end of the catheter. In addition, the conductor wire acts as a safety chain to ensure that the tip assembly remains on the catheter shaft while being used in an EP procedure.

The piezoelectric transducer 24 has an outer diameter that is just slightly less than the catheter body 18 and the tip electrode 22 so that the diameter is the same when the matching layer is applied. The transducer 24 may be composed of a ceramic crystalline material. The outer 32 and inner 30 surfaces of the transducer have a thin film, electrically conductive metallic coating (not shown) such as gold, silver, or nickel disposed thereon to provide transducer excitation electrodes. A first electrically conductive transducer wire 92 is soldered to the metallic coating disposed on the outer surface 32 of the transducer at the proximal end thereof. A second electrically conductive transducer wire 94 is soldered to the metallic coating disposed on the inner surface 30 of the transducer at the distal end thereof. Each of the transducer wires has an electrically insulative jacket (not shown) that insulates the respective wires along their lengths to prevent short circuiting.

The band electrode 26 is generally a thin walled ring having an outer diameter substantially the same diameter as the catheter body 18, and the tip electrode 22. The inner diameter of the band is sized for mounting over the shoulder 74 of the base 58. The electrode band is electrically conductive and may be formed of platinum or gold or other materials. An electrical sensor lead 96 is provided and has its distal end bonded to the inner surface of the band, for instance by soldering or weldment. The electrode sensor lead 96 has an electrically insulative jacket (not shown) that insulates the lead along its length.

The catheter body 18 is formed with a longitudinal inner lumen 97 that extends the entire length of the body to its proximal end. The distal extremity of the catheter body is formed with an annular mounting hole 99 having an inner diameter sized for receipt of the mounting stem 82 of the base 58.

When the distal end of the catheter 10 is assembled, the proximal end of the electrode sensor lead 96 of the electrode band 26 is passed inwardly through the electrode lead bore 78 of the base 58 and extended in a proximal direction out through the inner bore 60 thereof. The electrode band is thereafter assembled over the shoulder 74 of the base into contact with the abutment plate 80. The band is adhesively bonded to the shoulder, for instance using epoxy, to securely affix the band electrode to the base.

A pair of elastomeric O-rings 98 and 100 are provided to center the piezoelectric transducer 24 on the mounting base 58 at the catheter distal end and fix it in position. They also vibrationally isolate the piezoelectric transducer 24 from the other components of the catheter 10. The first O-ring 98 is positioned in the second retainer groove 70 of the flange 68 at the proximal end of the neck 66. The second O-ring 100 is disposed within the first retainer groove 64 at the head 62 of the base.

The O-rings 98 and 100 may be composed of a low durometer material such as a silicone based polymer that provides sufficient high frequency vibration isolation characteristics while providing sufficient hardness such that the ultrasonic vibrations generated from the piezoelectric transducer 24 are not unduly damped.

The piezoelectric transducer 24, having the temperature sensing devices 28 mounted thereto, is then mounted to the base 58. The first transducer wire 92 at the distal end of the transducer is received inwardly through the electrode lead bore 78 beneath the electrode band 26 and directed in a proximal direction through the inner bore 60 of the base. The second transducer wire 94 at the distal inner end of the transducer, along with the respective temperature sensor lead pairs 35 of the respective temperature sensing devices 28 are guided inwardly into the sensor lead bores 71 and 72 of the neck 66 of the base 58. The cylindrical transducer 24 is then mounted over the O-rings 98 and 100 and the neck of the base. The proximal end of the transducer is spaced a short distance from the electrode band 26 and an electrically insulative spacer bead 102 (FIG. 2) of adhesive/sealant is applied between the band 26, base 58, and transducer 24 to seal the space between the transducer 24 and the electrode band 26 and affix the transducer 24 in position. The adhesive/sealant is of a low durometer, biocompatible adhesive/sealant and may be composed of a silicone-based polymer having sufficient vibrational isolating and electrical insulating characteristics.

The proximal end of the tip conductor 88 of the tip electrode 22 is then received within the distal end of the inner axial bore 60 of the base 58 and the mounting post 84 of the tip electrode pressed into the distal end of the inner bore 60. An adhesive, such as epoxy, bonds the mounting post within the inner bore 60 of the base. The proximal surface of the tip electrode is spaced a short distance from the distal end of the piezoelectric transducer 24 and a second electrically insulative spacer bead 104 of adhesive/sealant is applied between the tip electrode 22, base 58, and transducer 24 to seal the space between the transducer and the tip electrode affixing the transducer in position. This adhesive/sealant is also a low durometer, bio-compatible material having sufficient vibrational isolating and electrical insulating characteristics. The combination of the two internal O-rings 98 and 100 and the two adhesive spacing and sealing beads 102 and 104 at either end of the piezoelectric transducer optimize the transfer of acoustic energy from the transducer to the tissue.

To complete the assembly of the distal end 20 of the catheter 10, the proximal ends of the temperature sensor lead pairs 35, electrode sensing lead 96, transducer wires 93, 94 and the tip electrode conductor wire 88 are gathered together and directed into the distal end of the inner lumen 97 of the catheter body 18. The mounting stem 84 of the base 58 is pressed into the mounting hole 99 of the catheter body and fixedly securely thereto, for instance by an epoxy adhesive. The proximal ends of the sensing lead pairs, tip electrode conductor wire, electrode sensing lead, and transducer wires 92 and 94 are connected to an electrical connector of a manipulation handle (not shown) at the proximal end of the catheter body. They may be used for operative connection to temperature signal processing, mapping, and ultrasonic ablation operating systems.

The adhesive/sealant beads 102 and 104 provide a liquid seal that prevents blood and other fluids from reaching the underside of the piezoelectric transducer 24 and entering the inner lumen 97 of the catheter body 18. This also protects the various electrically conductive leads and wires contained within the catheter from short circuit by body fluids. Additionally, the adhesive rings electrically insulate the electrode band 26, transducer 24 and tip electrode 22 from each other to prevent short circuiting.

In an alternative embodiment shown in FIG. 6, a piezoelectric transducer 108 is formed in a different configuration. Some reentrant pathways may be located in positions where a side-fire catheter cannot reach. In such cases, an end-fire catheter configuration may be successfully used. Additionally, an end-fire catheter may also be used for more precise ablation procedures where thin but deep lesions are preferred.

In this embodiment, the transducer 108 has a hollow cylindrical portion defining a mounting flange 110 and has an integral, generally hollow, convex-shaped tip to result in a bullet-shaped appearance. The convex tip may be a paraboloid or a hemisphere or other shapes. By having the integral mounting flange 110 as shown, the transducer 108 is easier to mount to the tip of the catheter in comparison to previous designs having only a hemispherical-shaped transducer. Additionally, it can be more accurately and easily mounted on the distal tip because of the larger surface area of the mounting flange and the use of an O ring 143. This larger surface area for mounting also provides a larger surface area for the application of an adhesive to attach the tip to the catheter shaft. Improved sealing of the inner volume of the transducer should result.

The outer diameter of the flange 110 of the piezoelectric transducer 108 is sized to conform to the outer diameter of the catheter body 18. As shown, the distal-most end of the hemispherical tip 112 of the transducer 108 is formed with an axially aligned sensor bore hole 114. The sensor holes are formed by the ultrasonic machining technique described above.

The inner 116 and outer 118 surfaces of the transducer 108 are plated or coated with an electrically conductive coating (not shown), such as gold, silver, or nickel to provide transducer excitation electrodes.

A first transducer wire 120 is bonded to the metallic coating disposed on the outer surface 118 of the transducer at the proximal end of the mounting flange 110. A second transducer wire 122 is bonded to the metallic coating disposed on the inner surface 116 of the tip 112 of the transducer. The wires are bonded to the respective surfaces by electrically conductive solder or other means to provide electrical continuity. Each of the transducer wires has an electrically insulative jacket (not shown) that insulates the respective wire along its length to prevent short circuiting.

The piezoelectric transducer 108, in this embodiment is constructed for mounting to the distal end 20 of the catheter body 18 through the use of a generally cylindrical mounting member or base 124. In this embodiment, the base has a distally projecting cylindrical mounting neck 126 formed at the proximal end thereof with a larger diameter abutment plate 128. The mounting neck is of smaller diameter than the inner diameter of the transducer flange 110. The outer diameter of the abutment plate 128 is sized to conform to the outer diameter of the catheter body 18. The proximal end of the abutment plate is formed with an axially projecting mounting stem 130 sized for snug receipt within the mounting hole 99 at the distal end of the catheter body 18. The base 124 is also formed with an axial through bore 132 sized substantially the same diameter as the central inner lumen 97 of the catheter body 18. A transducer wire bore hole 134 is formed from the outer surface of the mounting neck to the through bore 132 for receipt of the first transducer wire 120 therein. The base may be composed of an electrically insulative material such as VLTEM.

To assemble the convex piezoelectric transducer 108 onto the distal end 20 of the catheter body 18, a thermocouple sensor 136 such as that shown in FIG. 3 is first formed as described above. The temperature sensor lead pair 138 is directed through the inner lumen of the sheath (not shown) disposed within the axial sensor bore hole 114 of the convex transducer so that the lead pair is disposed within the inner volume of the transducer. The thermocouple end of the lead pair is bonded within the axial sensor bore hole so that the thermocouple is disposed generally flush with the outer surface 118 of the transducer. The thermocouple is bonded within the sensor bore hole using an appropriate adhesive sealant. The adhesive is shaped into a raised mound having a rounded crown 140 slightly above the outer surface of the transducer, the periphery of the crown having a diameter greater that the diameter of the sensor bore hole 114. The adhesive is cured to securely affix the thermocouple 136 in position in relation to the outer surface and the sensor bore hole of the transducer.

Once the adhesive is cured, the crown 140 protects the temperature sensing device 136 from damage and prevents the thermocouple thereof and sensor lead 138 from being pulled inwardly through the sheath after assembly. Furthermore, the adhesive crown 56 permits mounting of the thermocouple flush with the outer surface of the transducer and provides a liquid seal that prevents blood and other fluids that may come into contact with the distal end of the catheter from reaching the underside of the piezoelectric transducer 108 through the transducer bore hole 114.

To further assemble the hemispheric piezoelectric transducer 108 onto the distal end 20 of the catheter, the first transducer wire 120 is directed inwardly through the radial transducer wire bore 134 and the second transducer wire 122 and the temperature sensor lead 138 are gathered together and directed through the axial bore 132 of the mounting base 124. An O ring 143 is mounted on the base 124 to center and support the transducer 108 when it is mounted on the base.

The proximal end of the mounting flange 110 of the transducer 108 is then disposed over the mounting neck 126 of the base 124. The O ring assists in disposing the transducer in concentric alignment with the neck 126. Because the inner diameter of the mounting flange is larger than the outer diameter of the mounting neck, adhesive/sealant 144 is applied between the two as well as in the space 146 between the abutment plate 128 of the base and the mounting flange 110. The adhesive/sealant conforms with the outer diameter of the flange 110. The transducer wire bore 134 may also be filled with the adhesive/sealant 144.

The adhesive sealant 144 is of a low durometer, biocompatible polymer that securely affixes the transducer to the mounting neck 126 of the base and has sufficient vibrational isolating and electrical insulating characteristics. The adhesive sealant seals the interior of the catheter body 18 from the entry of bodily fluids that may cause undesirable transducer damping or possible short circuiting.

The respective transducer wires 120 and 122 and the temperature sensor lead 138 are then directed through the inner lumen 97 of the catheter body 18 to the proximal end of the catheter. The mounting stem 130 of the base is then pressed into the mounting hole 99 of the distal end 20 of the catheter body and affixed therein using an appropriate epoxy, for instance. The proximal ends of the sensing leads 130 and transducer wires 114 and 116 are connected to an electrical connector of a manipulation handle connector (not shown) for operative connection to a temperature measurement processing system and transducer operating system.

When the convex transducer 108 is in operation, the adhesive 144 between the mounting flange 110 and the mounting neck 126 provides minimal damping at the hemispherical tip 112 of the transducer because no adhesive is in contact with the inner surface thereof to cause such damping.

Referring to FIG. 7, a side-fire application of the catheter 10 illustrated in FIGS. 2 and 5 is shown. The distal tip 22 and band electrode 26 may be used for mapping purposes to locate an aberrant endocardial tissue site on the endocardial wall 16 of the heart chamber. Once the site 16 has been targeted, the distal end 20 of the catheter 10 is positioned against the targeted endocardial site 16 in a parallel orientation as shown in FIG. 7 to perform an ablation procedure. For optimum ablation effectiveness, the distal end of the catheter is oriented such that one longitudinal side of the cylindrical piezoelectric transducer 24 contacts the target tissue site. In this orientation, the clinician may activate the piezoelectric transducer to ablate the target endocardial tissue adjacent the transducer.

When activated for ablation, the cylindrical transducer 24 radiates ultrasonic energy at a selected frequency radially outwardly to the endocardial wall 16 to ablate the target tissue. Because there are a plurality of temperature sensors 28 and they are located substantially at the outer surface of the cylindrical transducer, the temperature sensors are able to sense the temperature of the ablated tissue, adjacent flowing blood and the surface temperature of the transducer itself very rapidly. By monitoring sensor outputs or by processing them in other ways, the temperature of the ablation site may be determined.

Referring now to FIG. 8 for an end-fire application, the catheter having the hemispherical transducer 108 at its distal tip is illustrated. The hemispherical tip transducer 108 configuration may be useful in certain applications where the aberrant target tissue is located at a position of the heart chamber not conducive to use of the catheter having the cylindrical transducer 24 of FIG. 7. Due to the contours of the heart chamber, the cylindrical transducer may be too large to fully contact the tissue along its longitudinal side and may therefore limit the cylindrical transducer's effectiveness.

In the perpendicular orientation shown in FIG. 8, the tip portion 112 of the convex transducer 108 and the distal tip temperature sensing device 136 are in contact with the target tissue of the endocardial wall 16. In this configuration, the tip transducer 108 is powered to ablate the target tissue. The convex piezoelectric transducer 108 shown may result in a relatively thin but deep lesion. Because the temperature sensing device 136 is in direct contact with the ablated tissue site, a direct indication of the temperature thereof is provided and thus the operation of the transducer may be more precisely and accurately controlled to maintain the temperature within limits.

In either of the catheter configurations shown in the figures, having the temperature sensing devices 28, 136 disposed in sensor bore holes 34, 114 formed in the piezoelectric transducer 24, 108 itself provides a desirable temperature sensing configuration. Because the thermocouple of the sensing device is disposed at the periphery of the transducer, a more accurate and faster temperature sensing response is provided. In addition, the chances of having a sensor in close proximity to the endocardial ablation site provides the clinician with a greater ability to control tissue and blood heating during the ablation procedure minimizing adverse effects to the patient. The temperature sensing devices 28 offer a more rapid temperature sensing response indication of the endocardial ablation site and the flowing blood adjacent the ablation electrode so that ablation procedures can be more accurately and positively controlled.

Furthermore, the mounting means and adhesive/sealant configurations between the distal end of the catheter body and the particular piezoelectric transducer provide a secure mounting arrangement while preventing undesirable leakage of bodily fluids into the catheter body as well as reduced damping of the transducer.

While particular forms of the invention have been illustrated and described, various modifications can be made without departing from the spirit and scope of the invention. Accordingly, it is not intended that the invention be limited, except as by the appended claims.

What is claimed is:

1. A catheter comprising:

an elongated catheter tube having proximal and distal ends and an inner lumen extending the length of the tube;

an ultrasonic transducer mounted at the distal end of the catheter tube, the transducer having a wall with inner and outer surfaces, the transducer having a plurality of sensor holes formed completely through the wall of the transducer;

a temperature sensing device disposed within each sensor hole in the wall of the transducer; and an adhesive disposed over each sensor hole on the outer surface of the transducer to seal the hole and the respective temperature sensing device thereby sealing the temperature sensing device from contact with fluids exterior to the transducer.

2. The catheter of claim 1 further comprising a flexible sheath disposed in and in contact with the sensor hole in the wall of the transducer wherein;

the temperature sensing device is disposed within the sheath in the wall of the transducer; and the adhesive is disposed over the sensor hole on the outer surface of the transducer to seal the hole and disposed in contact with the interior of the sheath in contact with the temperature sensing device affixing the temperature sensing device and the sheath in the sensor hole and sealing the temperature sensing device from contact with fluids exterior to the sheath.

3. The catheter of claim 2 wherein:

the temperature sensing device comprises an electrical lead;

the flexible sheath has a length selected to be longer than the thickness of the wall of the transducer with the sheath disposed so that the extra length is disposed inside the transducer to provide a strain relief to the leads of the sensing device.

4. The catheter of claim 1 wherein the temperature sensing devices each comprises a thermocouple located substantially level with the outer surface of the transducer.

5. The catheter of claim 1 further comprising a matching layer disposed over the outer surface of the transducer, the properties of the matching layer selected to better match the ultrasonic transducer to tissue to which it may contact.

6. The catheter of claim 1 further comprising:

electrodes formed on the outer and inner surfaces of the transducer to conduct electrical signals to the transducer for excitation of the transducer; and electrode leads for conducting electrical signals to and from the electrodes.

7. The catheter of claim 1 wherein:

the catheter further comprises an internal mounting member;

the ultrasonic transducer is mounted to the internal mounting member by an elastomeric member that positions the transducer properly in relation to the catheter and isolates the transducer mechanically from the catheter so that transducer vibrations are not significantly damped.

8. The catheter of claim 7 wherein:

the transducer has a hollow, cylindrical form;

the mounting member comprises two elastomeric members spaced apart from each other to properly align the transducer in the catheter and to isolate the transducer mechanically from the catheter so that transducer vibrations are not significantly damped.

9. The catheter of claim 8 further comprising:

an end member and a shaft member;

a first spacing member disposed between the transducer and the shaft member; and a second spacing member disposed between the transducer and the end member;

wherein the first and second spacing members comprise a sealing and non-damping material that seals the interior of the catheter from external fluids and also isolates the transducer mechanically from the catheter so that transducer vibrations are not significantly damped.

10. The catheter of claim 1 wherein the wall of the cylindrical transducer comprises three sensor holes located 120 degrees apart.

11. A catheter comprising:

an elongated catheter tube having proximal and distal ends and an inner lumen extending the length of the tube;

a hollow, cylindrical piezoelectric transducer mounted at the distal end of the catheter tube, the transducer having a wall and inner and outer surfaces;

an internal mounting member;

one or more sensor holes formed completely through the wall of the transducer;

a temperature sensing device disposed within one or more of the sensor holes in the wall of the transducer; and wherein the cylindrical ultrasonic transducer is mounted to the internal mounting member by an elastomeric member that positions the transducer properly in relation to the catheter and isolates the transducer mechanically from the catheter so that transducer vibrations are not significantly damped.

12. The catheter of claim 11 wherein:

the mounting member comprises two elastomeric members spaced apart from each other to properly align the transducer in the catheter and to isolate the transducer mechanically from the catheter so that transducer vibrations are not significantly damped.

13. The catheter of claim 11 further comprising:

an end member and a shaft member;

a first spacing member disposed between the transducer and the shaft member; and a second spacing member disposed between the transducer and the end member;

wherein the first and second spacing members comprise a sealing and non-damping material that seals the interior of the catheter from external fluids and also isolates the transducer mechanically from the catheter so that transducer vibrations are not significantly damped.

14. The catheter of claim 11 further comprising:

an electrode formed on the outer surface of the transducer to conduct electrical signals to the transducer for excitation of the transducer;

an electrode lead for conducting electrical signals to and from the electrode;

wherein the electrode is selected and mounted to the transducer to receive electrical signals from outside the transducer and conduct those signals to the electrode lead.

15. The catheter of claim 11 further comprising:

a matching layer disposed over the outer surface of the transducer and over each sensor hole and sensing device, the properties of the matching layer selected to better match the ultrasonic transducer to tissue to which it may contact.

16. The catheter of claim 11 further comprising:

a thermally conductive adhesive disposed over each sensor hole on the outer surface of the transducer to seal the hole and the respective temperature sensing device thereby sealing the temperature sensing device from contact with fluids exterior to the transducer.

17. A catheter comprising:

an elongated catheter tube having proximal and distal ends and an inner lumen extending the length of the tube;

a mounting member disposed in the distal end; and a hollow, piezoelectric transducer having a convex shape with an integral mounting flange, the transducer having a wall and inner and outer surfaces;

wherein the integral mounting flange of the transducer is mounted at the distal end of the catheter tube on the mounting member distal to the catheter tube so that the transducer forms the distal tip of the catheter.

18. The catheter of claim 17 wherein the ultrasonic transducer is mounted to the mounting member by an elastomeric member that positions the transducer properly in relation to the catheter, seals the catheter from the entry of external fluids, and isolates the transducer mechanically from the catheter so that transducer vibrations are not significantly damped.

19. The catheter of claim 18 further comprising:

an electrode formed on the outer surface of the transducer to conduct electrical signals to the transducer for excitation of the transducer;

an electrode lead for conducting electrical signals to and from the electrode;

wherein the electrode is selected and mounted to the transducer to receive electrical signals from outside the transducer and conduct those signals to the electrode lead.

20. The catheter of claim 19 further comprising:

a sensor hole formed completely through the wall of the transducer;

a temperature sensing device disposed within the sensor hole in the wall of the transducer; and a thermally conductive adhesive disposed over the sensor hole on the outer surface of the transducer to seal the hole and the respective temperature sensing device thereby sealing the temperature sensing device from contact with fluids exterior to the transducer.

21. A catheter comprising:

an elongated catheter tube having proximal and distal ends and an internal mounting member at the distal end of the tube;

a hollow, cylindrical piezoelectric transducer mounted axially around the internal mounting member of the catheter tube, the transducer having a wall with inner and outer surfaces;

an elastomeric member positioned between the internal mounting member of the catheter tube and the inner surface of the wall of the transducer, said elastomeric member positioning the transducer properly in relation to the catheter and isolating the transducer mechanically from the catheter so that transducer vibrations are not significantly damped.

22. The catheter of claim 21, wherein the elastomeric member comprises one or more elastomeric O-rings.

23. The catheter of claim 22, wherein the catheter tube further comprises:

one or more retainer grooves in the internal mounting member;

wherein the O-rings are mounted in said retainer grooves.

24. The catheter of claim 21, further comprising:

one or more sealant beads positioned between the piezoelectric transducer and the catheter tube.

* * * * *

UNITED STATES PATENT AND TRADEMARK OFFICE
CERTIFICATE OF CORRECTION

PATENT NO. : 5,606,974
DATED : Mar. 4, 1997
INVENTOR(S) : Thomas M. Castellano, Robert C. Hayzelden, Tracy D. Maahs It is certified that error appears in the above-indentified patent and that said Letters Patent is hereby corrected as shown below:

Column 1, line 11, after "S-A", replace "n", with --node--.

Column 2, line 61, replace "pan", with --part--.

Column 5, line 47, after "platinum", change "10" from bold type face to normal type face.

Signed and Sealed this

Twenty-fifth Day of November, 1997

Attest:

BRUCE LEHMAN

*Attesting Officer*  *Commissioner of Patents and Trademarks*